US00PP29816P3

(12) United States Plant Patent
Danziger

(10) Patent No.: US PP29,816 P3
(45) Date of Patent: Nov. 6, 2018

(54) ***CALIBRACHOA* PLANT NAMED 'DCALCOCHLA'**

(50) Latin Name: *Calibrachoa hybrida*
Varietal Denomination: DCALCOCHLA

(71) Applicant: Gavriel Danziger, Beit Dagan (IL)

(72) Inventor: Gavriel Danziger, Beit Dagan (IL)

(73) Assignee: Danziger 'DAN ' Flower Farm (IL)

( * ) Notice: Subject to any disclaimer, the term of this patent is extended or adjusted under 35 U.S.C. 154(b) by 0 days.

(21) Appl. No.: 15/530,798

(22) Filed: Feb. 28, 2017

(65) Prior Publication Data

US 2018/0249617 P1 Aug. 30, 2018

(51) Int. Cl.
*A01H 5/02* (2018.01)

(52) U.S. Cl.
USPC ..... Plt./413

(58) Field of Classification Search
USPC ..... Plt./413

CPC . A01H 5/02; A01H 5/00; A01H 5/025; A01H 5/12
See application file for complete search history.

(56) References Cited

PUBLICATIONS

Plant Peddler Growing Opportunities 2017, retrieved on Mar. 14, 2018, retrieved from the Internet at https://cld.bz/users/user-9rLuGIj/2017-Plantpeddler-Catalog/30, 2 introductory pages, 1-3, 28, 68-69, back cover page. (Year: 2017).*

Upov Pluto Plant Variety Database 20180308 *Calibrachoa* Dcalcochla, retrieved on Mar. 14, 2018, retrieved from the Internet at https://www3.wipo.int/pluto/user/en/index.jsp, one page. (Year: 2018).*

* cited by examiner

*Primary Examiner* — June Hwu
(74) *Attorney, Agent, or Firm* — Cassandra Bright

(57) ABSTRACT

A new and distinct *Calibrachoa* cultivar named 'DCALCOCHLA' is disclosed, characterized by a compact, mounded plant habit. Plants produce an abundance of large fuchsia colored flowers with a yellow center and throat, darker veins, and white margins. Plants have short internodes and are distinctively day length neutral. The new variety is a *Calibrachoa*, normally produced as an outdoor garden or container plant.

2 Drawing Sheets

Figure 1:
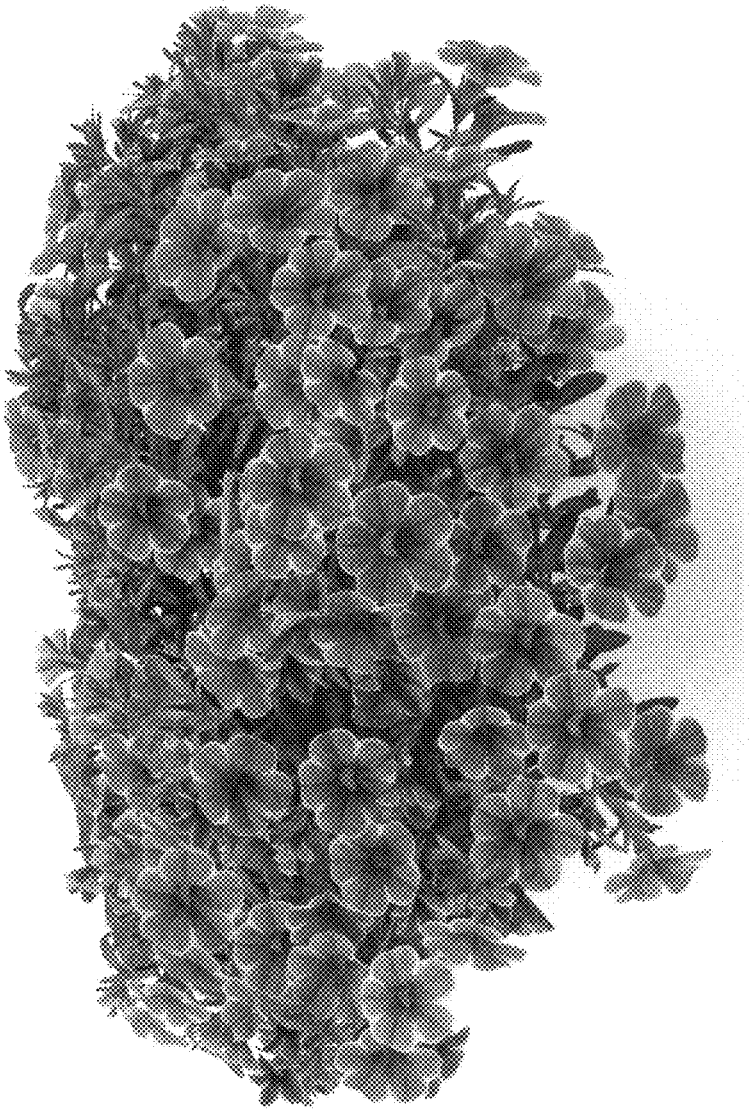

Latin name of the genus and species: *Calibrachoa hybrida.*

Variety denomination: 'DCALCOCHLA'.

BACKGROUND OF THE INVENTION

The new *Calibrachoa* cultivar is a product of a planned breeding program conducted by the inventor, Gavriel Danziger in Moshav Mishmar Hashiva, Israel. The objective of the breeding program was to produce new *Calibrachoa* varieties. The cross resulting in this new variety was made during April of 2014.

The seed parent is the unpatented, propriety variety referred to as *Calibrachoa* 'cv. 13-3598'. The pollen parent is the unpatented, propriety variety referred to as *Calibrachoa* 'cv. 12-3202'. The new variety was discovered in November of 2014 by the inventor in a group of seedlings resulting from the parental crossing, in a greenhouse in Moshav Mishmar Hashiva, Israel.

Asexual reproduction of the new cultivar 'DCALCOCHLA' was first performed by terminal vegetative cuttings during November of 2014, at a greenhouse in Moshav Mishmar Hashiva, Israel. Subsequent propagation by has shown that the unique features of this cultivar are stable and reproduced true to type in successive generations.

SUMMARY OF THE INVENTION

The cultivar 'DCALCOCHLA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DCALCOCHLA' These characteristics in combination distinguish 'DCALCOCHLA' as a new and distinct *Calibrachoa* cultivar:

1. Mounded and compact growth habit.
2. Early flowering.
3. Fuchsia flower color with darker veins, white margin, yellow center and throat.
4. Short internode length
5. Abundance of flowers.
6. Day length neutral flowering.

PARENT COMPARISON

Plants of the new cultivar 'DCALCOCHLA' are similar to plants of the seed parent in most horticultural characteristics, however, plants of the new cultivar 'DCALCOCHLA' differ in the following;

1. The seed parent has a trailing growth habit, the new variety is mounded.
2. The new variety has a bright fuchsia flower with dark veins, yellow center and a white margin, the seed parent is dark pink.
3. The new variety has a shorter internode length than the seed parent.

Plants of the new cultivar 'DCALCOCHLA' are similar to plants of the pollen parent in most horticultural characteristics however, plants of the new cultivar 'DCALCOCHLA' differ in the following;

1. The pollen parent has a trailing growth habit whereas the new variety is mounded
2. The new variety has more branches than the pollen parent.
3. Pollen parent flower color is pink, the new variety flower color is fuchsia with darker veins, white margin and yellow center and throat.
4. The pollen parent produces a moderate quantity of flowers, the new variety has an abundance of flowers.

COMMERCIAL COMPARISON

Plants of the new cultivar 'DCALCOCHLA' can be compared to the patented commercial variety *Calibrachoa* 'Uscali51' U.S. Plant Pat. No. 14,874. These varieties are similar in most horticultural characteristics; however, 'DCALCOCHLA' differs in the following:

1. The new variety begins blooming earlier than this comparator.
2. the new variety is day length neutral, this comparator is day length sensitive.
3. Flower color of the new variety is fuchsia with darker veins, white margin and yellow center and throat.

Plants of the new cultivar 'DCALCOCHLA' can also be compared to the unpatented commercial variety *Calibrachoa* 'Calipetite White Improved'. These varieties are similar in most horticultural characteristics; however, 'DCALCOCHLA' differs in the following:

1. Flower color of the new variety is fuchsia with darker veins, white margin and yellow center and throat. Flower color of this comparator is white.
2. Flower size of the new variety is larger.
3. Plants of the new variety are more vigorous than plants of this comparator.

BRIEF DESCRIPTION OF THE PHOTOGRAPHS

The accompanying photograph in FIG. 1 illustrates in full color a typical plant of 'DCALCOCHLA' grown in a greenhouse, in Moshav Mishmar Hashiva, Israel.

Figure 2:
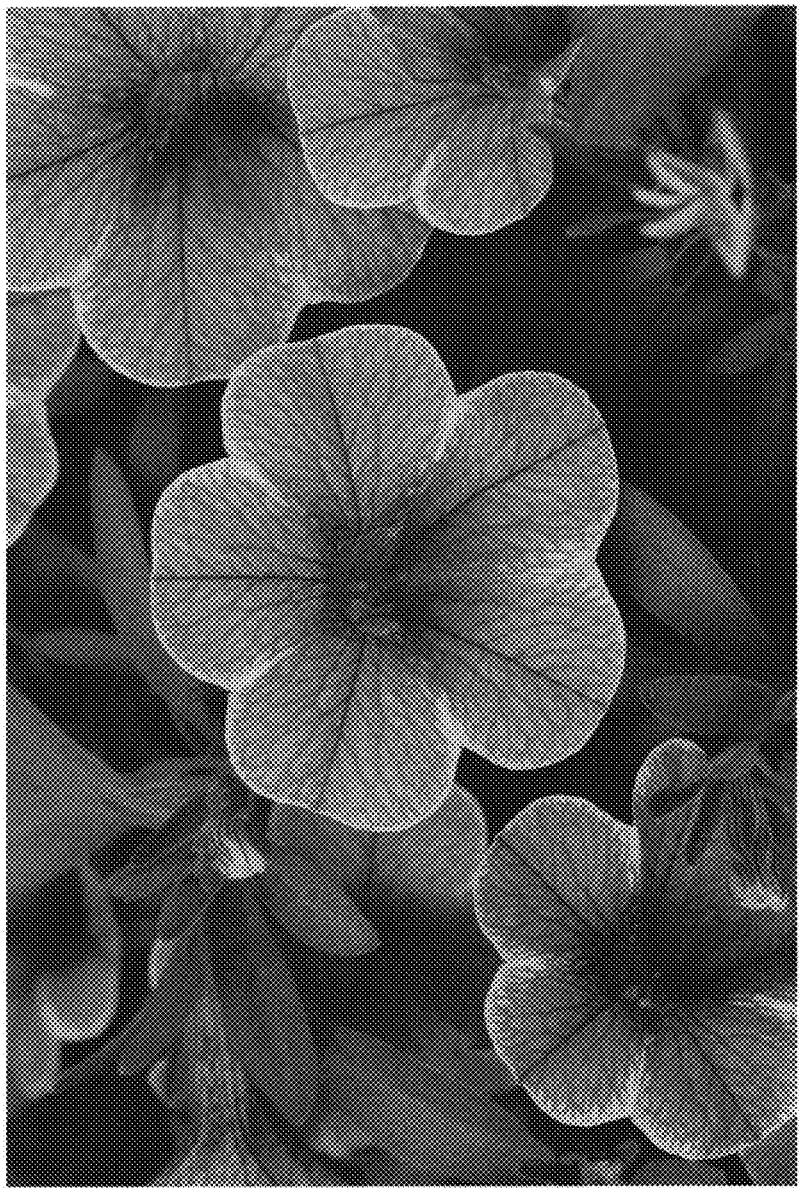

FIG. 2 illustrates in full color a close up of typical flowers of 'DCALCOCHLA'. Age of the plant photographed is approximately 100 days from a rooted cutting in a 30 cm pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DCALCOCHLA' plants grown in greenhouse in Moshav Mishmar Hashiva, Israel, under natural lighting. Measurements were taken during April of 2015. The plants were approximately 60 days from a rooted cutting in a 13 cm pot. The growing temperature ranged from 15° C. to 28° C. during the days, 15° C. to 20° C. during the nights. Measurements and numerical values represent averages of typical plant types.

Botanical classification: *Calibrachoa hybrida* 'DCALCOCHLA'.

PROPAGATION

Time to initiate roots: 10 to 15 days at approximately 18° C.

PLANT

Growth habit: Mounded.
Pot size of plant described: 13 cm.
Height: About 14 cm to top of flowering plane.
Plant spread: about 30 to 40 cm.
Growth rate: Moderate.
Branching characteristics: Very well branched.
Length of primary lateral branches: About 16 to 18 cm.
Diameter of lateral branches: About 0.2 to 0.3 cm.
Quantity of primary lateral branches: 11 to 13.
Characteristics of primary lateral branches:
*Form*.—Cylindrical, somewhat laterally compressed.
*Diameter*.—0.2 to 0.3 cm.
*Color*.—RHS Yellow-Green 146B.
*Texture*.—Hispid.
*Strength*.—Strong, flexible.
Internode length: About 1.5 to 2.0 cm.
Root description: Densely fibrous. Brown, not accurately measured with an R.H.S. chart.

FOLIAGE

Leaf:
*Arrangement*.—Alternate.
*Quantity*.—Approximately 55 per branch.
*Average length*.—3.8 cm.
*Average width*.—1.0 cm.
*Shape of blade*.—Elliptic.
*Apex*.—Rounded.
*Base*.—Acuminate.
*Margin*.—Entire.
*Texture of top surface*.—Glabrous.
*Texture of bottom surface*.—Scabrous.
*Color*.—Young foliage upper side: RHS Green 137C. Young foliage under side: RHS Green 138B. Mature foliage upper side: RHS Green 137A. Mature foliage under side: RHS Green 137D.
*Venation*.—Type: Pinnate. Venation color upper side: RHS Green 137A. Venation color under side: RHS Green 138C.
*Petiole*.—Length: about 0.3 to 0.5 cm. Diameter: about 0.15 cm. Color: RHS Green 138B. Texture: Glabrous.

FLOWER

Natural flowering season: Spring, Summer and Autumn in Beit Dagan, Israel.
Days to flowering from rooted cutting: About 20 to 30 days.
Inflorescence and flower type and habit: Axillary, single flower, salverform shape, upward and outwardly facing.
Rate of flower opening: 2 to 3 days from bud to fully opened flower.
Flower longevity on plant: 4 to 7 days.
Approximate quantity of flowers per plant: About 50.
Persistent or self-cleaning: Self-cleaning.

Bud:
*Shape*.—Ovoid.
*Length*.—About 0.3 cm.
*Diameter*.—About 0.2 cm.
*Color*.—RHS Yellow-Green 145B.

Flower size:
*Diameter*.—About 3.5 to 4.0 cm.
*Length*.—About 3.5 cm.
*Flower tube diameter at distal end*.—About 1.0 cm.
*Flower tube diameter at proximal end*.—About 0.3 cm.

Petals:
*Length from throat*.—About 1.6 to 1.8 cm.
*Flower lobing*.—Strong.
*Width*.—About 1.7 to 1.9 cm.
*Veins, upper surface*.—Moderate to strong.
*Quantity*.—5.
*Veins, inner corolla tube*.—Strong.
*Texture*.—Glabrous.
*Apex*.—Truncate.
*Margin*.—Entire.

Color:
*When opening*.—Upper surface: Main surface Red-Purple 68B and towards base 61B. Veins 61A, margin White N155C. Lower surface: Main surface Red-Purple 68B and towards base 61B. Veins 61A, margin White N155C.
*Fully opened*.—Upper surface: Main surface Red-Purple 68B and towards base 61B. Veins 61A, margin White N155C. Lower surface: Main surface Red-Purple 68B and towards base 61B. Veins 61A, margin White N155C. Flower throat (inside): RHS Yellow 8B. Flower throat, vein: RHS Red-Purple 61B. Flower tube (outside): RHS Yellow 8C. Flower tube, vein: RHS Red-Purple 61B. Petal color, fading to: Main surface Red-Purple 63A and 63C. Veins 61A, margin White N155C.

Calyx/sepals:
*Quantity per flower*.—5.
*Shape*.—Lanceolate.
*Length*.—About 1.5 cm.
*Width*.—About 0.2 to 0.3 cm.
*Apex*.—Rounded.
*Base*.—Fused.
*Margin*.—Entire.
*Texture*.—Glabrous.
*Color*.—Upper Surface: RHS Yellow-Green 147B. Lower Surface: RHS Yellow-Green 147B.

Peduncle:
*Length*.—About 1.5 cm.
*Diameter*.—About 0.2 cm.
*Color*.—RHS Yellow-Green 144B.
*Texture*.—Pubescent.
*Orientation*.—45 degrees.

Fragrance: None.

REPRODUCTIVE ORGANS

Stamens:
*Number*.—5.
*Filament length*.—Average range 2 to 5 mm.

Anthers:
*Length*.—About 0.1 cm.
*Shape*.—Globose.
*Color*.—RHS Yellow 9C.
*Pollen*.—Color: RHS Yellow 9D. Quantity: Moderate.

Pistil:
*Number*.—1.
*Length*.—About 1.1 cm.
*Style*.—Length: About 0.7 cm. Color: RHS Yellow-Green 147D.
*Stigma*.—Shape: Oblate. Color: RHS Yellow-Green 147B. Ovary Color: RHS Yellow-Green 147D.

OTHER CHARACTERISTICS

Seeds and fruits: About 30 dark brown, rounded seeds of about 0.5 mm diameter, per one brown, conical capsule. Seed color close to 200A, capsule color close to 200D.

Disease/pest resistance: Typical to known *Calibrachoa* varieties. Neither resistance nor susceptibility to the normal diseases and pests of *Calibrachoa* have been observed. Pests common to *Calibrachoa* include Aphids and thrips. Typical diseases are *Botrytis* and *Pythium*.

Temperature tolerance: 5° C. to 30° C.

Drought tolerance: No tolerance for drought.

What is claimed is:

1. A new and distinct cultivar of *Calibrachoa* plant named 'DCALCOCHLA' as herein illustrated and described.

* * * * *